United States Patent [19]

Forare et al.

[11] Patent Number: 5,383,449
[45] Date of Patent: * Jan. 24, 1995

[54] VENTILATOR CONTROL SYSTEM FOR MIXING AND DELIVERY OF GAS

[75] Inventors: Lester Forare, San Diego; Paul Fennema, Fallbrook; Roger Gagne, Carlsbad, all of Calif.

[73] Assignee: Puritan-Bennett Corporation, Carlsbad, Calif.

[*] Notice: The portion of the term of this patent subsequent to Apr. 5, 2011 has been disclaimed.

[21] Appl. No.: 128,546

[22] Filed: Sep. 28, 1993

Related U.S. Application Data

[63] Continuation of Ser. No. 2,690, Jan. 11, 1993, Pat. No. 5,299,568, which is a continuation of Ser. No. 793,242, Nov. 12, 1991, abandoned, which is a continuation of Ser. No. 370,018, Jun. 22, 1989, abandoned.

[51] Int. Cl.$^6$ .................... A62B 9/02; G05B 1/00
[52] U.S. Cl. .................... 128/205.11; 128/205.24
[58] Field of Search .............. 128/204.21, 204.22, 128/205.11, 205.13–205.17, 204.28, 205.24

[56] References Cited

U.S. PATENT DOCUMENTS

| | | | |
|---|---|---|---|
| 3,283,754 | 11/1966 | Goodner | 128/205.14 |
| 3,593,735 | 7/1971 | Reiker | 128/204.22 |
| 3,669,134 | 6/1972 | Dobritz | 128/203.25 |
| 3,741,208 | 6/1973 | Jonsson et al. | 128/145.6 |
| 3,817,085 | 6/1974 | Stubbs | 128/204.22 |
| 3,840,006 | 10/1974 | Buck et al. | 128/204.21 |
| 3,848,617 | 11/1974 | Dray | 128/205.11 |
| 4,022,234 | 5/1977 | Dobritz | 137/7 |
| 4,023,587 | 5/1977 | Dobritz | 137/88 |
| 4,072,148 | 2/1978 | Munson et al. | 128/205.11 |
| 4,340,044 | 7/1982 | Levy et al. | 128/205.15 |
| 4,345,612 | 8/1982 | Koni et al. | 128/203.25 |
| 4,380,233 | 4/1983 | Caillot | 128/205.11 |
| 4,561,287 | 12/1985 | Rowland | 73/23 |
| 4,576,159 | 3/1986 | Hahn et al. | 128/205.16 |
| 4,602,635 | 7/1986 | Ruiz-Vela et al. | 128/204.22 |
| 4,651,729 | 3/1987 | Rae | 128/204.22 |
| 4,702,242 | 10/1987 | Broddner et al. | 128/205.13 |
| 4,905,685 | 3/1990 | Olsson et al. | 128/204.21 |
| 5,299,568 | 4/1994 | Forare et al. | 128/205.24 |

FOREIGN PATENT DOCUMENTS

| | | |
|---|---|---|
| 117699A3 | 9/1984 | European Pat. Off. |
| 256171A1 | 2/1988 | European Pat. Off. |
| 2079984A | 1/1982 | United Kingdom |

*Primary Examiner*—Kimberly L. Asher
*Attorney, Agent, or Firm*—Fulwider Patton Lee & Utecht

[57] ABSTRACT

The ventilator control system for delivery respiratory gas to a patient involves an apparatus which includes a pressure sensor for measuring the pressure within a gas containment vessel, the control of the flow of respiratory gas into the containment vessel responsive to pressure within the containment vessel, and the control of the outflow of respiratory gas responsive to changes in pressure in the containment vessel. Both the inflow of gas to a receiver tank and outflow of respiratory gas are responsive to modes of breathing being provided to a patient.

8 Claims, 4 Drawing Sheets

VENTILATOR CONTROL SYSTEM FOR MIXING AND DELIVERY OF GAS

This is a continuation of application Ser. No. 08/002,690, filed Jan. 11, 1993, now U.S. Pat. No. 5,299,568, which was a continuation of U.S. Ser. No. 07/793,242 filed Nov. 12, 1991, now abandoned which was a continuation of U.S. Ser. No. 07/370,018 filed Jun. 22, 1989, now abandoned.

BACKGROUND OF THE INVENTION

1. Field of the Invention

This invention relates generally to breathing ventilators, and more particularly to a pnuematically driven, electronically controlled ventilator system for mixing gas proportions and delivering breathing gas for either controlled or spontaneous breaths.

2. Prior Art

Conventional breathing ventilators generally provide a positive over pressure of breathing gas to a patient, and may provide respiratory gas under pressure in a predetermined manner responsive to pressure variations in the breathing pattern of the patient, or may operate to supply a predetermined volume of respiratory gas to a patient in a controlled manner for each breath. The breathing gas is generally provided with an elevated concentration of oxygen. An oxygen concentrator having a reservoir for receiving the oxygenated product gas, including a sensor for monitoring withdrawal of the product gas from the reservoir, and a microprocessor for determining the minimum time for charging of the gas to provide a product gas with a selected oxygen concentration at the sensed rate of withdrawal is described in U. S. Pat. No. 4,561,287 (Rowland). A plurality of canisters with molecular sieve beds for absorbing nitrogen provide the oxygenated gas to the reservoir, and a valve mechanism is provided for directing air from a compressor to alternate sieve beds. Another system for mixing the two gases in predetermined proportions involves the introduction of two gases via separate inlets into a pressure vessel receiving the first gas up to a first pressure, and then receiving the second gas up to a second pressure, to provide the proper proportioning of the mixed gases. This system is described in U.S. Pat. Nos. 4,022,234 and 4,023,587 (Dobritz). The mixed gases are withdrawn until the initial pressure within the receiving vessel is reached, at which time the withdrawal of gas is interrupted, and the mixing cycle is again commenced. The feedback control of the rate of flow and pressure of breathing gas to a patient by an inspiration servounit is also described in U.S. Pat. No. 3,741,208 (Jonsson, et al.)

It would be desirable to provide a ventilator system which can mix the constituent gases in a respiratory gas in a manner responsive to pressure within the respiratory gas contained in the receiving vessel, and responsive to the various modes of breathing for which the respiratory gas is being provided.

SUMMARY OF THE INVENTION

The present invention provides a system and a method for delivery of respiratory gas to a patient from a containment vessel, which includes measurement of the quantity of gas within the containment vessel, control of the flow of respiratory gas into the containment vessel responsive to pressure within the containment vessel, and control of the outflow of respiratory gas responsive to changes in pressure or volume in the containment vessel.

Briefly and in general terms, the ventilator system for delivery of respiratory gas to a patient comprises a containment vessel; an inlet means connecting the containment vessel with a source for respiratory gas; and outlet means connecting the containment vessel with a patient; a sensor for sensing the quantity of gas within the containment vessel; means for controlling the inflow of respiratory gas to the containment vessel in response to the quantity of gas sensed within the containment vessel; and means for controlling the outflow of respiratory gas in response to changes in the quantity of gas in the containment vessel. Similarly, the method for delivering respiratory gas to a patient from the containment vessel involves the steps of measuring the quantity of gas within the vessel; introducing gas into the containment vessel up to a predetermined quantity level; withdrawing gas from the vessel; measuring the quantity of gas within the vessel periodically to determine a change in pressure over time; and controlling the withdrawal of gas from the vessel in a predetermined manner responsive to the changes in the quantity of the gas within the vessel over time.

In a preferred embodiment of the system of the invention, means are also included for determining the rate of outflow of gas from the vessel based upon the pressure or volume sensed within the vessel, means for comparing the outflow rate with a predetermined value, and means for adjusting the outflow based upon this comparison. The inlet flow control also preferably includes means for comparing the pressure or volume within the vessel with a predetermined value, and a valve mechanism for filling the vessel responsive to this comparison. In another preferred embodiment of the invention, means are included for determining a predicted pressure or volume in the containment vessel based upon a predicted rate of change in the vessel, with the valve mechanism for filling the vessel being responsive to a predicted pressure or volume. The containment vessel also preferably contains a means for reducing temperature fluctuations in the respiratory gas contained within the vessel.

In the method of the invention, the control of withdrawal of gas from the containment vessel preferably includes comparing a measure of the change in the quantity of gas in the vessel, such as the pressure or volume change, with a corresponding predetermined value and adjusting the outflow in the outlet to reduce the difference between the measured change and the predetermined value. The method preferably includes comparing the measured quantity of gas in the containment vessel with a predetermined threshold value, and introducing gas into the vessel when the quantity of gas falls below the threshold value. Another preferred embodiment of the method involves determining a predicted quantity of gas in the vessel based upon a predicted rate of change in the vessel, comparing the predicted value with a predetermined value, and filling the vessel with gas when the predicted value falls below the predetermined threshold value. The respiratory gas is also preferably composed of a plurality of component gases, and the method preferably includes determining the estimated number of molecules or quantity of gas within the vessel based upon the gas pressure or volume in the vessel, determining the number of moles of each component gas required to fill the vessel to a predetermined fill level with a particular ratio of component gases; for each component gas, determining a pressure change value and pressure increase value in the vessel corresponding to the number of moles required to fill the vessel with the predetermined ratio of component gases; and filling the vessel with each component gas up to the pressure increase value.

Two basic breath types are supported by the ventilator and method of the invention. A mandatory breath pattern is supported, in which the physical characteristics of the breath supplied to the patient are completely specified by operator selected settings. The physical characteristics selected by the operator may include a wave form, tidal volume, peak inspiratory flow, composition, such as the oxygen concentration, and the cycle interval. A mandatory breath pattern can be initiated by an independent operator, or even by the patient.

A spontaneous breath pattern is also supported by the invention. A spontaneous breath is one in which the flow of inspiratory gas and tidal volume are determined solely by the patient effort. The composition of the respiratory gas, however, is determined by the value of the predetermined parameter of oxygen concentration. Respiratory gas flow to the patient is triggered by fluctuations in the airway pressure, and can be controlled by operator-selected settings of positive end expiratory pressure (PEEP) and sensitivity. A continuous positive airway pressure (CPAP) is provided. "Sensitivity" is the pressure level below PEEP that a patient must produce in order to trigger a patient initiated mandatory breath, or a spontaneous breath from the ventilator. Mandatory breaths can be initiated by the ventilator according to the parameter settings, the operator, or the patient. Ventilator initiated breaths are delivered at a constant cycle interval determined by the operator selected value for respiratory rate. Operator initiated breaths are one time events whose occurrence the operator determines by manual controls. Patient initiated breaths are delivered whenever a patient effort reduces the airway pressure below PEEP by an amount equal to the operator selected value for sensitivity.

The invention also provides for precise control of oxygen concentration in the breathing gas. Gas measurement is based upon the ideal gas law, which states that the product of gas pressure and volume is proportional to the product of the number of moles and temperature of the gas, or $$PV = NRT$$

where
P = absolute pressure of the gas;
V = gas container volume;
N = number of moles of gas;
R = the universal gas constant; and
T = absolute temperature of the gas.

Thus, the number of moles of gas in a fixed volume container can be determined indirectly by measuring the container volume, the gas pressure, and the gas temperature. A simple extension of this law implies that if gas is added or removed from the container, the pressure will change by a proportional amount;

$$\Delta P = \Delta NRT/V \qquad (1)$$

In addition, two ideal gases occupying the same space behave according to Dalton's law of partial pressures:

$$P = (N1 + N2)RT/V \qquad (2)$$

The mixing control algorithm is based upon equations 1 and 2. From (1), the number of gas molecules injected into the bottle is proportional to the measured pressure change:

$$\Delta N = \Delta PV/TR \qquad (3)$$

Thus, by proper calibration of the container, a pressure change measurement reads directly as moles of the fixed volume container, of gas injected, and can be used for gas mixed control. From (2) the number of moles of each gas in the respiratory gas containment vessel can be calculated from the mole ratios and pressure in the containment vessel:

$$NA = mix*PV/TR \qquad (4)$$

$$NO = (1 - mix)*PV/TR \qquad (5)$$

To fill the containment vessel to a desired mixture, the number of moles or molecules of each gas initially in the containment vessel is estimated by applying (4) and (5). The desired number of moles or molecules for each gas can be calculated by applying these equations for a desired mixture and pressure, and the pressure differential for each gas can be computed and converted to pressures using equation (3). Precise amounts of gas can be introduced into the containment vessel by sequentially injecting each gas to these pressure values. Similar calculations of the mixture and quantity of gas within the vessel may be performed for vessels with a volume which can change, either where the pressure is held fixed or where it is also subject to change.

This approach provides several significant advantages over other "batch type" mixing systems. Rapid mixing changes are possible since solenoids can be actuated independently, for example, to increase oxygen concentration, and an oxygen solenoid can be used exclusively for several cycles until the desired mixture is reached. In addition, high precision mixing is possible since a pressure transducer and a volume detector can provide extremely accurate, reliable gas pressure measurements, allowing for continuous mixture readjustment to correct for any variations that may result from mechanical valves. For example, if the fill solenoid valve happened to stick open for a brief time after it was signaled to close, the resulting pressure increase would be higher reflecting the additional amount of gas admitted. This variation is accommodated since the mix is determined from the measured pressure or volume change and so the amount of gas to admit in the next fill will be less.

Other aspects and advantages of the invention will become apparent from the following detailed description and the accompanying drawings, illustrating by way of example the features of the invention.

DETAILED DESCRIPTION OF THE INVENTION

As is shown in the drawings for purposes of illustration, the invention is embodied in a ventilator control system having a separate inlet flow path for each pressurized gas, connected to an electrically operated solenoid valve for each gas. The outlet of each of the gas solenoid valves that make up the gas mixture is connected to a containment vessel, or tank, such that as each solenoid valve is energized, the gases are combined in the tank. The containment vessel is a gas receiver tank or bottle that is filled by the flow of gas from one or more inlet conduits. Pressure may be monitored by a precision pressure transducer connected to the tank, and a containment vessel outlet port is connected by a gas flow path to an electrically operated flow control valve. In the method of the invention, gas pressure or volume within the vessel is measured, and from this information and the proportions of oxygen and other gases in the tank initially, the initial gas proportions are determined. The tank filling target pressures or volumes are determined, from a user defined parameter of oxygen concentration, and from the initial tank gas proportions, and each gas solenoid is actuated in turn to fill the tank from the initial level to the target levels. During the tank fill period the outlet flow control valve is closed, but once the gas proportioning fill cycle is complete, the outlet flow control is energized as required to provide the flow of precisely proportioned oxygen gas mixture to a patient. When the flow of gas out of the tank depletes the quantity of gas to a predetermined minimum, the cycle of proportional refilling is repeated.

In accordance with the present invention, there is provided a ventilator system for the delivery of respiratory gas to a patient comprising a containment vessel, inlet means to connect the containment vessel in fluid communication with a source for respiratory gas; outlet means to connect the containment vessel in fluid communication with a patient; sensor means to sense a measure of the quantity respiratory gas in the containment vessel; inlet flow control means to control the flow of respiratory gas 1 through the one inlet means in a predetermined manner responsive to the quantity of gas sensed in the containment vessel; and outlet flow control means to control the flow of respiratory gas through the outlet means in a predetermined manner responsive to changes in the quantity of gas sensed in the containment vessel over a period of time.

The present invention also provides for a method for delivering respiratory gas to a patient from a containment vessel; inlet means to connect the containment vessel in fluid communication with a source of respiratory gas; sensor means to sense a measure of the quantity of respiratory gas in the containment vessel; means to control the flow of respiratory gas through the inlet means; and outlet flow control means to control the flow of respiratory gas through the outlet means; comprising the steps of measuring the quantity of gas within the vessel; introducing the gas into the vessel through the inlet means until a predetermined quantity level in the vessel is reached; withdrawing the gas from the vessel through the outlet port; measuring the quantity of gas within the vessel periodically to determine a change in the quantity of gas over time; and controlling the withdrawing of gas from the vessel in a predetermined manner responsive to changes in the quantity of gas sensed in the containment vessel over a period of time.

Figure 1:
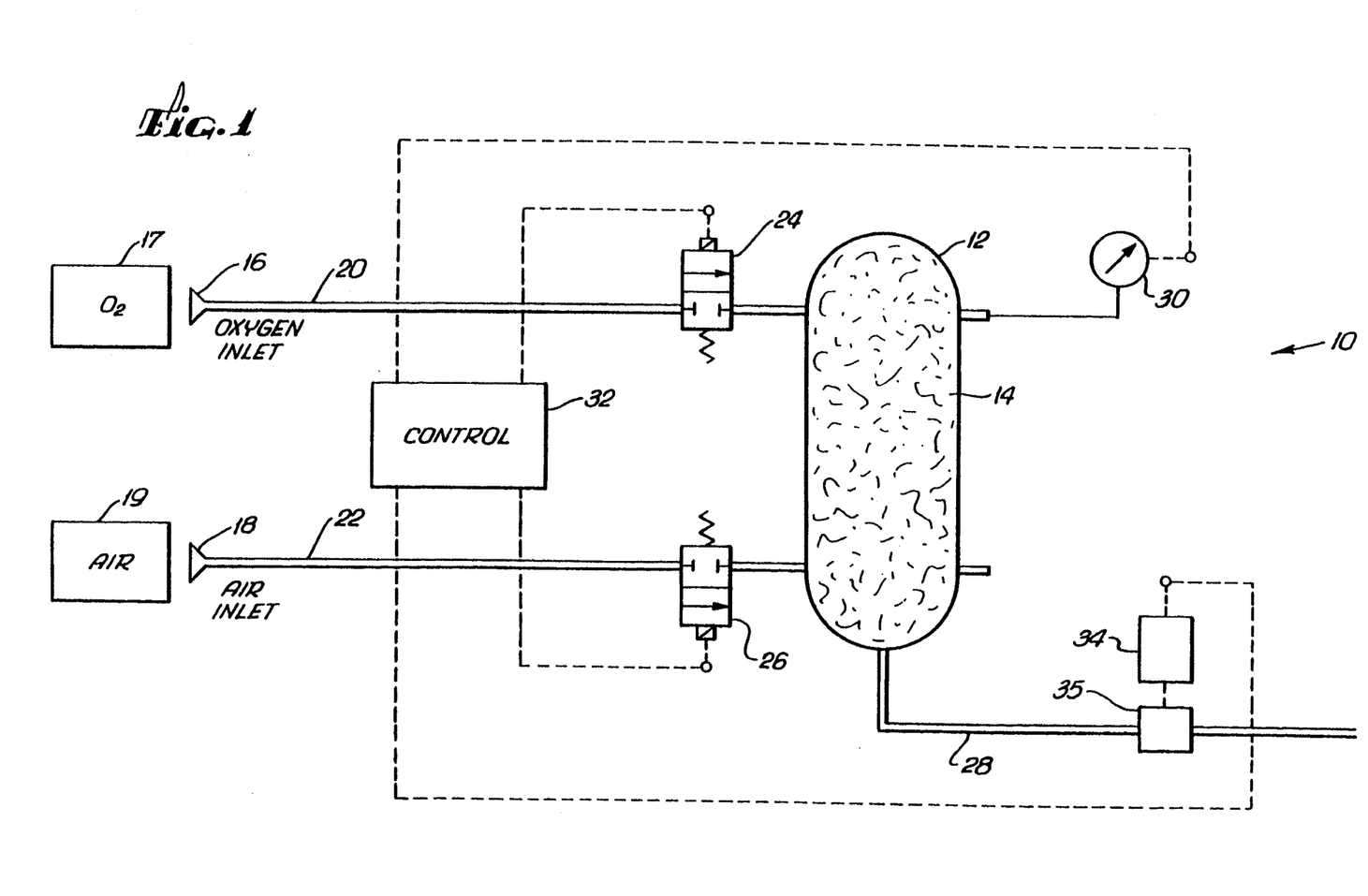
FIG. 1 is a simplified schematic diagram of the ventilator control system.

With reference to FIG. 1, the ventilator pneumatic control system 10 includes a receiver tank 12, which is in one currently preferred embodiment a rigid, fixed wall, pressure containment vessel, typically of approximately 2 liters in volume. Copper wool material 14 completely fills the interior volume of the tank, typically taking up to 2 percent of the tank volume. The copper wool, having a high specific heat value, ensures that the gas compression and decompression is relatively isothermal, during the filling and emptying cycles. Other similar material for reducing temperature fluctuations in the gas contained within the vessel may also be provided. The containment vessel may alternatively comprise a piston chamber, or a bellows-type of chamber, in which volume is adaptable to provide a variable capacity, with pressure being essentially constant, or in which volume and pressure are both variable, and both pressure and volume are monitored.

The receiver tank preferably has an oxygen inlet port 16 connected to an oxygen supply source 17. Similarly, the receiver tank also preferably includes an air inlet port 18 connected to an air supply source 19. The oxygen and air supply sources may simply be high pressure tanks of oxygen and air, and the air supply source may also be an air compressor. Other conventional sources of pressurized oxygen and air in hospital settings would also be appropriate. Alternatively, the air inlet line and oxygen inlet line may join to provide a premixing of the gases before they enter the containment vessel.

An oxygen supply conduit 29 preferably conveys oxygen from the oxygen inlet port to the tank, and an air supply conduit 22 conveys air to the receiver tank. The oxygen inlet line also has a solenoid valve 24 normally in a closed position, which can be energized by the electronic control system to supply pressurized oxygen to the receiver tank. Similarly, the air supply line includes a solenoid valve which can be energized by the electronic control system to provide pressurized air to the receiver tank.

Also connected to the receiver tank are an outlet conduit 28 for supplying respiratory gas from the receiver tank to the patient, and a pressure sensing pressure transducer 30. The electronic control means 32, preferably including a microprocessor for controlling all of the functions of the ventilator control system, is connected to the oxygen solenoid valve, the air solenoid valve, the pressure sensor at the vessel, and an outlet solenoid valve control 34, which functions to control the adjustable inspiration servovalve 35 in the outlet conduit.

Figure 2:
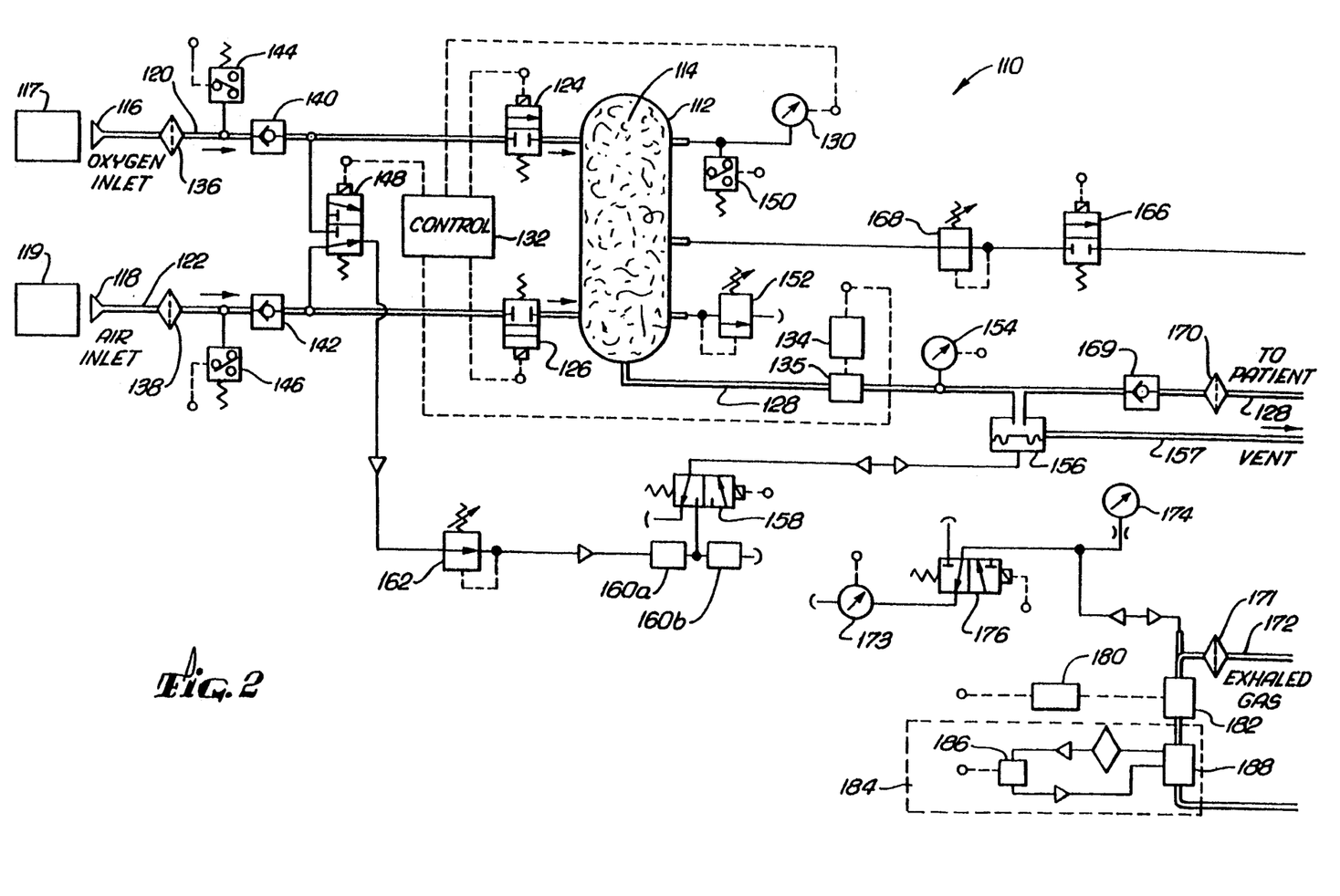
FIG. 2 is a detailed schematic diagram of the ventilator control system.

Referring to FIG. 2 those elements bearing reference numerals 110 through 134 correspond to elements bearing reference numerous 10 to 34, respectively. In the preferred mode of the invention, the oxygen inlet conduit also includes a filter 136 for the oxygen gas, and the air inlet conduit includes a filter 138 for the compressed air. Check valves 140 and 142 are also provided in the oxygen and air inlet conduits, and an oxygen pressure switch 144 and an air pressure switch 146 are connected near the gas inlet ports for low pressure gas supply monitoring. A crossover solenoid 148 is also preferably connected in line between the oxygen inlet conduit and the air inlet conduit to provide the ventilator with an alternate source of oxygen pressure should the normal respiratory gas system fail. The pressure switch 150 is connected to the receiver tank near the tank pressure sensor, and is used to electrically test the validity of the pressure transducer. A relief valve 152 is also connected to the receiver tank, and is used to relieve any over pressure conditions which may occur due to system or component failure.

Ventilator breathing gas flow is monitored by a second pressure sensor, the absolute pressure transducer 154 connected to the respiratory gas outlet conduit to the patient. Measurements made by the outflow absolute pressure transducer are used to determine patient system occlusion and atmosphere pressure and is also used to monitor validity of pressure readings in the patient breathing circuit. A safety relief valve 156 is also provided on the respiratory gas flow line, which serves to vent excessive pressure in the respiratory gas outflow to the vent 157. A safety valve solenoid 158 and restrictors 160a and 160b are also connected in line with the safety regulator, connected in fluid communication with the crossover solenoid, to form the basics of the safety system to provide air to the patient should the normal ventilator air system fail. The safety relief valve thus serves the dual purpose of venting excess pressure, and admitting ambient air to the respiratory gas outflow line to the patient, if necessary. The safety system also includes the outlet line check valve 164.

A ventilator nebulizer pressure source is provided by the nebulizer solenoid 166, which receives its pressure supply from the nebulizer 168 connected directly to the receiver tank. Nebulizer operation will not vary the controlled volume delivery, or breathing gas, oxygen percentage.

The ventilator output gas flow is also filtered by the outlet line filter 170, and is transported to the patient by patient tubing (not shown). Exhaled gas is returned to the ventilator by tubes (not shown), connected to a water trap 171 at the exhalation valve inlet 172 in the patient breathing circuit. Additional ventilator components are connected by a patient pressure port at the exhalation valve inlet. These are a third pressure sensor 173, a manometer 174, used to monitor patient system pressure, and an autozero solenoid 176, used for electronically zeroing the patient breathing circuit pressure sensor 173.

An exhalation servovalve 180 is used to control the patient exhaled gas flow that flows to the room. The exhalation servovalve is a direct drive servovalve driven by an electric force motor and controlled by the ventilator electronic system. The force motor is connected mechanically to the exhalation valve 182 of the breathing circuit. The spirometer 184 is a two-part system that consists of the mass flow sensor 186 and the flow venturi 188. The spirometry monitored by the mass flow sensor and the flow venturi provides gas flow measurements to the ventilator electronic system for both the patient data display and ventilator status alarm elements. The electronic system controls all of the functioning and inputs of the ventilator neumatic system, controlling oxygen inlet, air inlet and crossover solenoids, the inspiration servovalve and safety solenoid, as well as nebulizer solenoid and the autozero solenoid of the patient system pressure circuit. Each of the three pressure sensors and the flow sensor are also connected to the electronic system to provide data concerning the operation of the ventilator system.

Oxygen Air Proportioning

In normal ventilator operation, bottle pressure is atmospheric when the power is first turned on. After completing power-up procedures, the ventilation algorithms begin execution.

First, bottle pressure is measured and prior oxygen concentration is retrieved from memory. Applying (4) and (5), the number of molecules of each gas type is estimated, (NA, NO). Then, mix and volume commands from the keyboard are used to compute "bottle-full" pressure and the desired number of molecules of each gas type (NAD, NOD). The estimated number is subtracted from the desired number to give the number of molecules of each type to inject. Finally, equation (2) is applied to convert these values into equivalent pressure change values ($\Delta PA$, $\Delta PO$).

After establishing a pressure charge value for each gas, target pressure levels are calculated. The first solenoid valve is opened to charge the bottle and then closed when the pressure reaches its first target pressure. After a short pause the bottle pressure is measured and recorded. Next, the second solenoid is opened and then closed when the second target pressure level is reached. After a short pause the bottle pressure is measured and recorded again.

With a mix established based on precise solenoid actuation, the true mix is now even more accurately estimated using equations (4) and (5) and the intermediate pressure measurements. This estimate replaces the former mix stored in memory.

Inspiration follows and gas from the bottle is delivered to the patient through the servovalve until the desired volume is delivered (mandatory breath) or the patient triggers end-of-inspiration (spontaneous). In either case, the mixing algorithm reengages.

At this point, the alogrithm follows two different procedures depending on the therapist-selected mode. In the spontaneous mode, the current bottle pressure is compared to a threshold. Only when it falls below this threshold will a new mixing cycle begin, and the bottle is filled completely. If it is above the threshold, mixing will not yet be performed. This threshold approach is used to reduce mixing inaccuracy due to pressure measurement errors.

In the mandatory mode, bottle pressure for the next cycle is estimated based on current pressure and the volume to be delivered to the patient on the next cycle. Specifically, the predicted pressure change due to a single volume delivery is subtracted from the current pressure. This estimate is then compared to a threshold and if it falls below, a new mixing cycle is performed as before. If not, mixing is skipped. This approach ensures that bottle pressure is always maintained above the threshold required for nebulizer operation.

Example 1

Air/Oxygen Mix Control

Figure 3:
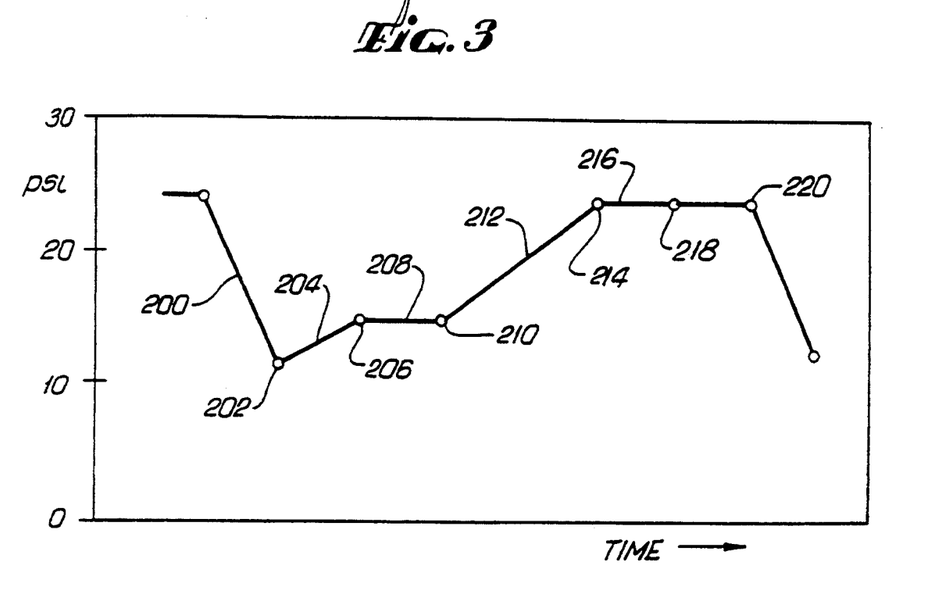
FIG. 3 is a graph of the air/oxygen mix control of example 1.

This example illustrates the events that compose a complete mix cycle. FIG. 3 shows bottle pressure vs. time during the mix process. Marked events are:
1. Gas is delivered to patient through servovalve (200).
2. Gas delivery completed, servovalve is closed (202)
   Bottle pressure is recorded.
   Previous mix is retrieved from memory.
   Current amount of each gas is estimated.

Keyboard entered mix command is retrieved from memory.
Desired bottle pressure is computed as follows:
  a. mandatory: add threshold, delivery pressure
  b. spontaneous: use maximum bottle pressure
Desired amount of each gas is calculated.
Amount of each gas to inject is obtained by subtraction.
3. Oxygen solenoid valve is opened (204).
  Pressure is monitored as oxygen is added.
4. Pressure reaches target for oxygen (206).
  Oxygen solenoid is closed.
5. A short pause allows pressure to settle (208).
6. Pressure is measured (210).
  Pressure change due to oxygen is calculated and recorded.
7. Air solenoid valve is opened (212).
  Pressure is monitored as air is added.
8. Pressure reaches target for air (214).
  Air solenoid is closed.
9. A short pause allows pressure to settle (216).
10. Pressure is measured (218).
  Pressure change due to air is calculated and recorded. New mix is estimated from air and oxygen pressure changes measured.
11. Inspiration starts and gas begins to flow to the patient (220).

Example 2

Refill Logic for Spontaneous Ventilation

Figure 4:
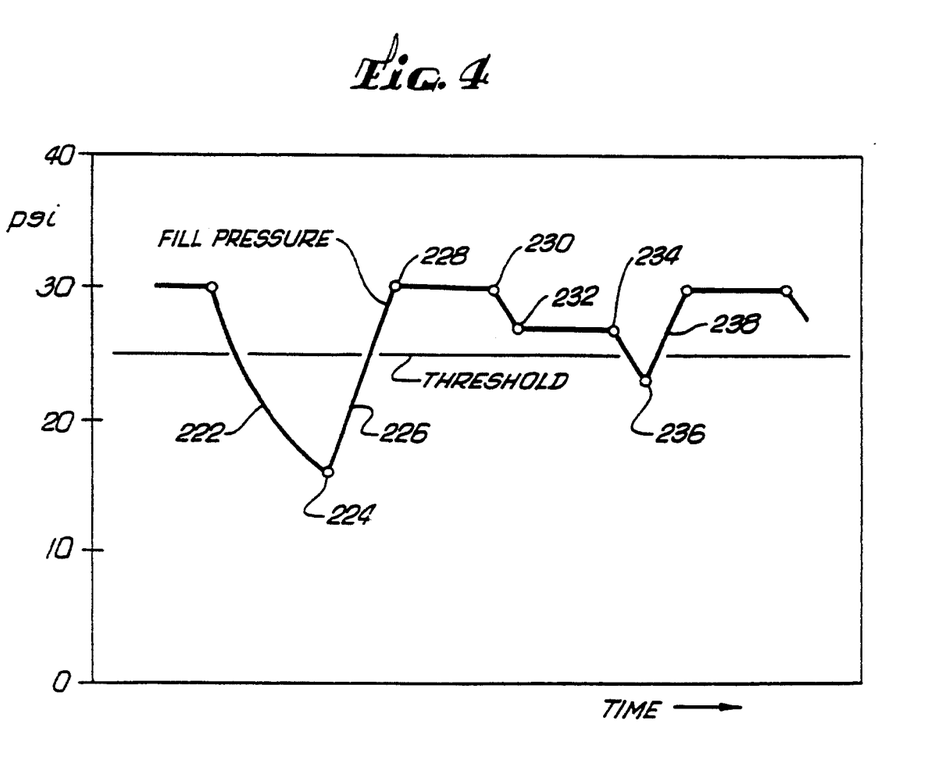
FIG. 4 is a graph of the receiver tank pressure for spontaneous ventilation (example 2)

Spontaneous breaths are controlled by the patient and therefore are not predictable in size. The bottle must be fully recharged after every significant breath to ensure a large breath demand can be met in the next inspiration. In addition, mix accuracy depends largely on ensuring significant refill pressure change, therefore a threshold is used to enforce a minimum pressure charge. A typical pressure history is illustrated in FIG. 4:

1. Patient inspires (222).
2. Patient terminates inspiration (224).
  Bottle pressure is recorded and compared to threshold.
  Pressure is below threshold so proceed to refill.
  Set target pressure to 30 psi.
3. Perform mix control as in Example 1 (226).
4. Pressure reaches 30 psi (228).
  Mix control finished.
  Wait for patient to inspire.
5. Patient inspires (230).
6. Patient terminates inspiration (232).
  Bottle pressure is recorded and compared to threshold.
  Pressure is above threshold so refill is not performed.
  Wait for patient to inspire.
7. Patient inspires (234).
8. Patient terminates inspiration (236).
  Bottle pressure is recorded and compared to threshold.
  Pressure is below threshold so proceed to refill.
  Set target pressure to 30 psi.
9. Perform mix control as in Example 1 (238).

Example 3

Refill Logic for Large Mandatory Breaths

Figure 5:
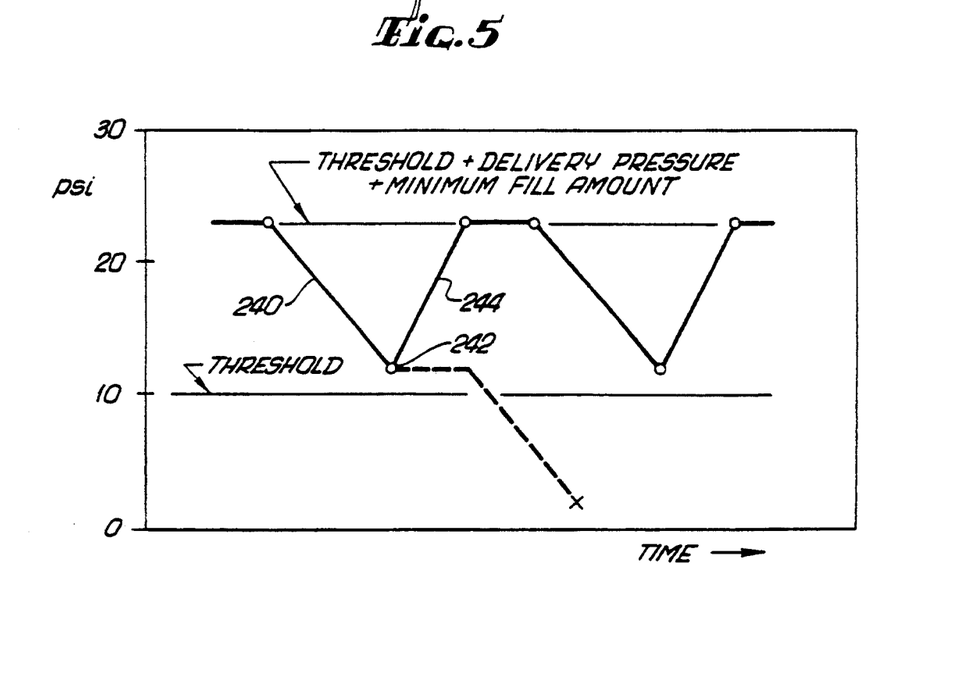
FIG. 5 is a graph of receiver tank pressure for large mandatory breaths (example 3)

Mandatory ventilation provides predetermined breath size and so the bottle need not be completely refilled after each inspiration. This provides the opportunity to operate at lower pressures where the servovalve exhibits better linearity for improved flow control. However, a minimum pressure threshold is used to ensure sufficient nebulizer pressure. The bottle pressure is always maintained above the threshold. A typical bottle pressure history for this case is illustrated in FIG. 5:

1. Gas is delivered to the patient (240).
2. Inspiration terminates as the desired volume is achieved (242).
  Bottle pressure is recorded.
  Forecast pressure after next breath.
  Pressure forecast is below threshold, proceed to refill.
3. Perform mix control as in Example 1 (244).

Since the volumes in this example are large, the pressure will always fall below the threshold and so refill will occur after each breath.

Example 4

Refill Logic for Small Mandatory Breaths

Figure 6:
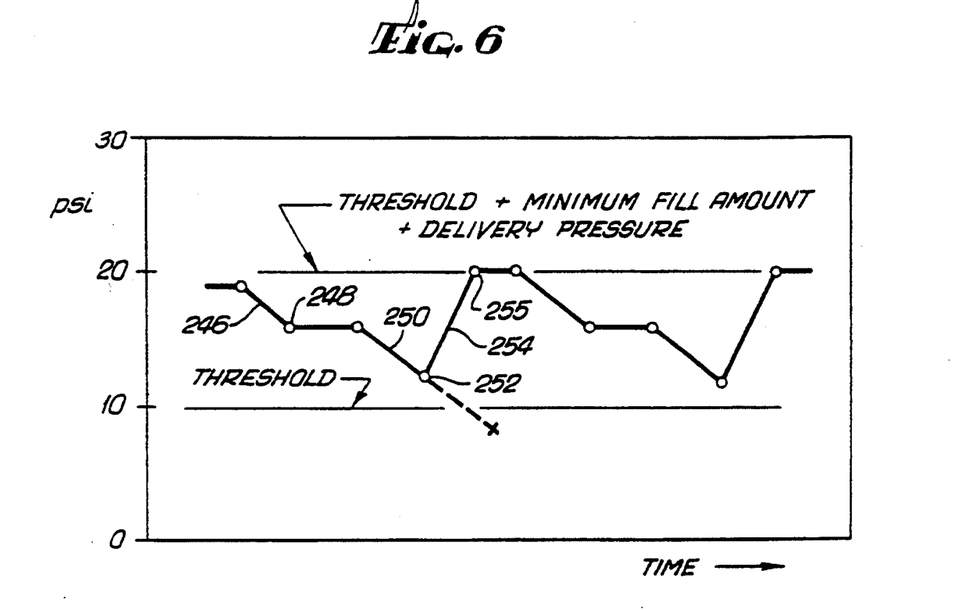
FIG. 6 is a graph of receiver tank pressure for small mandatory breaths (example 4).

Small mandatory breaths produce small changes is bottle pressure and so refill should not occur after each inspiration. This prevents both mix inaccuracy and solenoid valve wear. A good example is illustrated in FIG. 6:

1. Gas is delivered to the patient (246).
2. Inspiration terminates as the desired volume is achieved (248).
  Bottle pressure is recorded.
  Forecast pressure after next breath.
  Forecast is above threshold so refill is not performed.
3. Gas is delivered to the patient (250).
4. Inspiration terminates as the desired volume is achieved (252).
  Bottle pressure is recorded.
  Forecast pressure after next breath.
  Forecast is below threshold so proceed to refill.
5. Perform mix control as in Example 1 (254).
6. Mix control complete (256).
  Wait for next breath.

Controlled Volume Delivery

For volume limited, mandatory ventilation, the operator determines parameters of tidal volume, and peak flow required, and enters these parameters into the electronic control system, to enable the ventilator system to deliver the desired breath. The drive gas pressure for the ventilator is stored in the receiver tank. During the inspiratory phase, the oxygen inlet solenoid valve and the air inlet solenoid valve remain closed, and the receiver tank pressure sensor continuously monitors pressure or volume levels within the receiver tank. At the start of inspiration, the initial pressure in the receiver tank is received from the pressure sensor, and entered into the microprocessor system memory, and the respiratory gas outlet solenoid servovalve is activated to regulate flow to the patient.

For peak flow control, an electronically differentiated pressure signal from the receiver tank pressure transducer is used to determine the gas flow rate out of the receiver tank. This dp/dt signal is used by the electronic control system to feed a control loop to the inspiration servovalve and maintain the desired set flow rate. The absolute pressure transducer in the outlet conduit, located downstream of the inspiration servovalve, provides measurements for atmospheric pressure, and for detection of breathing circuit occlusions.

A square wave form of ventilator flow is the standard method of controlled volume delivery. Volume control is accomplished by direct pressure measurement of the starting and end pressures in the receiver tank, during the inspiratory phase of ventilation. Volume is indirectly determined from the pressure change in the receiver tank, according to the ideal gas law equations.

The spontaneous breathing mode of the ventilator is an important function of the ventilator of the invention. The responsiveness of the ventilator to patient demand breathing determines the quality of breathing. The ventilator control system will implement a proportional servovalve controlled, spontaneous breathing mode with the servocontrol loop on the patient pressure sensor 173, located in the exhalation system flow path of the patient tubing for best response to patient demands.

In the foregoing description, it has been demonstrated that the system and method of the invention allow for control of the flow of respiratory gas into a pressure containment vessel in a predetermined manner responsive to pressure within the containment vessel and the mode of delivery of respiratory gas to a patient. It is also significant that the system and method of the invention allow for control of the outflow of respiratory gas to a patient in a predetermined manner responsive to changes in pressure sensed in the containment vessel over a period of time, and based upon the mode of delivery respiratory gas to a patient.

Although a specific embodiment of the invention has been described and illustrated, it is clear that is susceptible to numerous modifications and embodiments within the ability of those skilled in the art and without the exercise of the inventive faculty. Thus, it should be understood that various changes in form, detail and application of the present invention may be made without departing from the spirit and scope of this invention.

I claim:

1. A ventilator system for the intermittent delivery of respiratory gas to a patient comprising:

a rigid, fixed wall pressure containment vessel;

first and second inlet ports connected to said vessel, with each said inlet, port being in fluid communication with corresponding first and second separate sources of first and second respective component gases to be combined in a desired ratio to form said respiratory gas, said component gases having an initial known ratio, with said first and second inlet ports having associated corresponding first and second inlet valves for individually controlling the flow of each said component gas through said inlet ports to said vessel;

outlet means to connect said vessel in fluid communication with the patient;

sensor means to determine onset and completion of inhalation by the patient, to sense the pressure of said respiratory gas in the containment vessel following said completion of inhalation by of the patient, and to generate a differentiated pressure signal representing a rate of change of pressure in said containment vessel over a period of time;

inlet flow control means to sequentially control the flow of said first component gas into said containment vessel in response to said determination of completion of inhalation by the patient through said first inlet port while said second inlet port is closed, and to control the flow of said second component gas through said second inlet port while said first inlet port is closed, in a desired ratio responsive to the pressure of gas sensed in the containment vessel, including means for determining a desired pressure change value for each said component gas in said containment vessel corresponding to the number of moles of each said component gas required to fill said vessel with said desired ratio of said component gases to a desired fill pressure based upon a total pressure and said initial known ratio of component gases in said vessel, and means for determining an actual ratio of said component gases in said respiratory gas in said vessel based upon sensed changes in pressure of said component gases introduced into said containment vessel; and outlet flow control means electrically connected to said sensor means to control the flow of said respiratory gas through the outlet means following said onset of inhalation in a predetermined manner responsive to said differentiated pressure signal based upon the rate of change in the pressure of gas sensed in the containment vessel.

2. The system of claim 1, wherein said outlet flow control means comprises means for determining the rate of outflow of said respiratory gas from said vessel responsive to said differentiated pressure signal from said sensor means, output comparison means for comparing said rate of outflow with a predetermined reference outflow value adapted to generate an error signal, and valve means in fluid communication with said outlet means operatively connected to said output comparator means to receive said error signal, and adapted to adjust said outflow to said predetermined outflow value in response to said signal.

3. The system of claim 1, wherein said inlet flow control means includes fill control means for comparing the pressure of gas in said vessel with a predetermined threshold pressure, responsive to said pressure of gas sensed by said sensor means, and adapted to generate a fill signal when the pressure of gas in said vessel falls below said threshold pressure valve, said first and second inlet valves being operatively connected to said fill control means for receiving said fill signal.

4. The system of claim 1, wherein said inlet flow control means includes means for determining a predicted pressure of gas in said vessel after a predicted next inhalation by the patient, based upon said sensed rate of change of pressure in said vessel, and fill control means for comparing said predicted pressure of gas with a predetermined pressure threshold value.

5. A method for intermittently delivering respiratory gas to a patient from a respirator by providing a rigid, fixed wall pressure containment vessel having first and second inlet ports, each of said inlet ports connecting the vessel in fluid communication with first and second separate sources of respective first and second component gases to be combined in said vessel in a desired ratio to form said respiratory gas, said respiratory gas in said vessel having an initial known ratio of said component gases; providing outlet means to connect the vessel in fluid communication with the patient; providing sensor means to sense the pressure of said respiratory gas in the containment vessel; and providing means to sequentially control the flow of said component gases through said inlet ports; and output flow control means to control the flow of said respiratory gas through said outlet means, said method further comprising the steps of:

determining onset and completion of inhalation by the patient;

measuring the pressure of gas within said vessel following said completion of inhalation by the patient;

determining pressure increase values for said first and second component gases in said vessel corresponding to the number of molecules of each said component gas required to fill said vessel with said desired ratio of said component gases to a desired fill pressure based upon the total pressure and said initial known ratio of component gases in said vessel;

sequentially filling said vessel with said component gases to said corresponding pressure increase values while measuring pressure in said containment vessel in response to said determination of completion of inhalation by the patient, by introducing said first component gas into said vessel through said first inlet port while said second inlet port is closed, and said second component gas through said second inlet port while said first inlet is closed according to said pressure change values until said fill pressure of gas in said vessel is reached;

measuring an actual pressure increase in said containment vessel for each said component gas introduced into said vessel;

determining the ratio of said component gases in said containment vessel based upon said initial known ratio of component gases in said vessel, said total pressure and said actual pressure changes for each said component gas introduced into said vessel;

withdrawing said gas from said vessel through said outlet means responsive to said determination of onset of inhalation;

measuring an outflow rate of change in the pressure of gas in the vessel over time and generating a differentiated pressure signal representing the outflow rate of change of pressure in said vessel over said period of time; and controlling said withdrawing of gas from said vessel in a predetermined manner responsive to said outflow rate of change in the pressure of gas sensed in said containment vessel.

6. The method of claim 5 wherein said step of controlling said withdrawing of gas comprises comparing said rate of change in the pressure of gas with a predetermined reference outflow value and generating an error signal representing the difference between said rate of change in the pressure of gas and said reference outflow value; and adjusting said outflow in said outlet in response to said error signal to reduce the difference between said rate of change in the pressure of gas and said reference outflow value.

7. The method of claim 5, further including the steps of: comparing said measured pressure of gas in said vessel with a predetermined threshold value; and introducing said first and second component gases into said vessel in said desired ratio when the pressure in said vessel falls below said threshold value and until the total pressure of said gas in said vessel reaches a predetermined upper limit.

8. The method of claim 5, further including the steps of:

determining a predicted pressure in said vessel after a predicted next inhalation of the patient based upon said sensed rate of change in pressure in said vessel over a predetermined period of time;

comparing said predicted pressure with a predetermined threshold pressure value; and filling said vessel with said gas when said predicted pressure falls below said predetermined threshold pressure value.

* * * * *